United States Patent
Harris

(10) Patent No.: US 7,253,305 B2
(45) Date of Patent: Aug. 7, 2007

(54) TERTIARY ALKYL ACETATE PREPARATION

(75) Inventor: Stephen H. Harris, Kennett Square, PA (US)

(73) Assignee: Lyondell Chemical Technology, L.P.

( * ) Notice: Subject to any disclaimer, the term of this patent is extended or adjusted under 35 U.S.C. 154(b) by 61 days.

(21) Appl. No.: 11/190,084

(22) Filed: Jul. 26, 2005

(65) Prior Publication Data

US 2007/0027337 A1    Feb. 1, 2007

(51) Int. Cl.
C07C 67/02    (2006.01)
(52) U.S. Cl. .................................... 560/234
(58) Field of Classification Search ............... 560/231, 560/234, 248, 265
See application file for complete search history.

(56) References Cited

U.S. PATENT DOCUMENTS

| 2,678,332 | A | 5/1954 | Cottle | 260/475 |
|---|---|---|---|---|
| 3,031,495 | A | 4/1962 | Young et al. | 260/497 |
| 3,053,887 | A | 9/1962 | Aries | 260/497 |
| 3,082,246 | A | 3/1963 | Chafetz | 260/497 |
| 3,172,905 | A | 3/1965 | Eckert | 260/497 |
| 3,173,943 | A | 3/1965 | Hess et al. | 260/497 |
| 6,417,412 | B1 | 7/2002 | Kahn et al. | 568/917 |
| 6,593,491 | B2 | 7/2003 | Murphy et al. | 560/240 |
| 6,770,790 | B1 | 8/2004 | Li et al. | 568/917 |
| 2002/0183544 | A1* | 12/2002 | Williams et al. | 560/231 |

OTHER PUBLICATIONS

Sheng et al., Huaxue Shijie (2000), 41(9), 476-475, See online Chemical Abstracts citation attached from CAPLUS, Columbus, OH, USA [retrieved on Jan. 31, 2006], Abstract No. 2000:782067.*
Fritz et al., Acid-catalyzed acetylation of organic hydroxyl groups, Anal. Chem. (1959), 31, 1808-12.*

* cited by examiner

Primary Examiner—Karl Puttlitz
(74) Attorney, Agent, or Firm—William C. Long

(57) ABSTRACT

Esters are formed by reaction of acetic anhydride with tertiary butyl or tertiary anyl alcohol in the presence of tertiary amine catalyst such as DMAP or NMI catalyst and acetic acid in amount sufficient to present catalyst degradation; in preferred practice a mixed acetic anhydride and acetic acid stream is recycled to the esterfication.

6 Claims, 1 Drawing Sheet

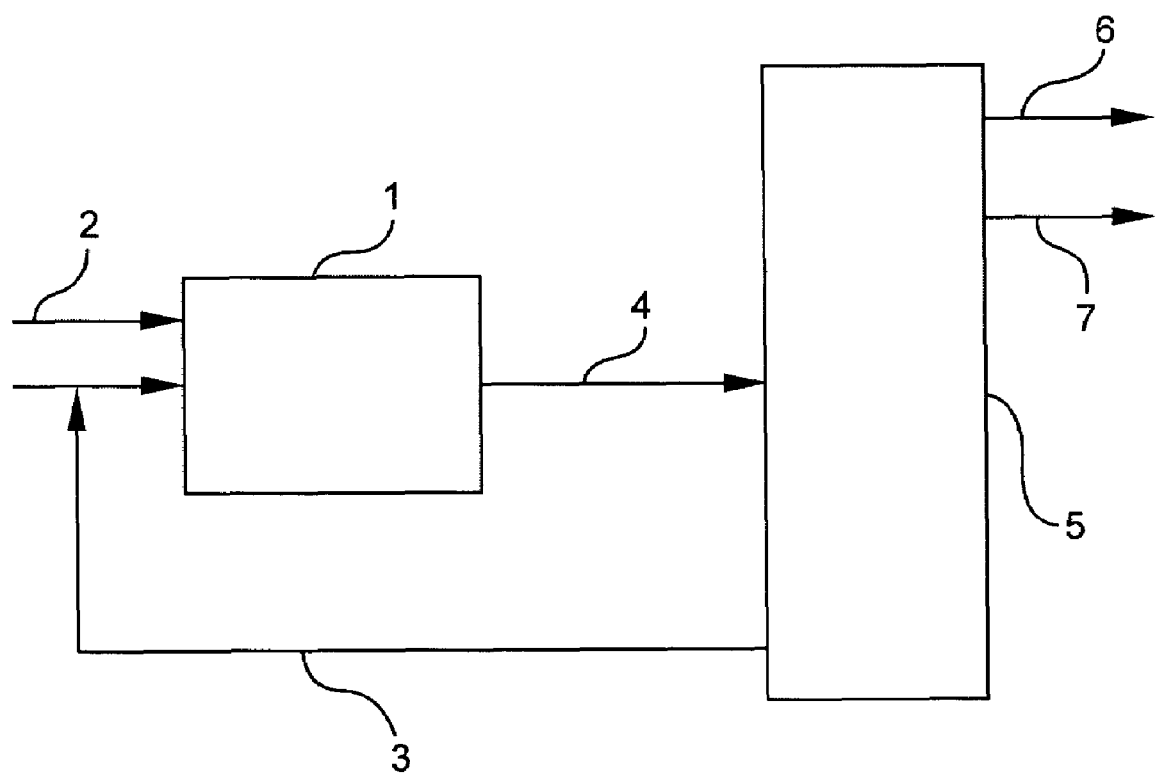

TERTIARY ALKYL ACETATE PREPARATION

FIELD OF THE INVENTION

The present invention relates to a process for the preparation of a tertiary alkyl acetate ester such as t-butyl acetate by catalytic reaction of the t-alkanol and acetic anhydride.

BACKGROUND OF THE INVENTION

Tertiary alkyl esters such as t-butyl acetate and t-amyl acetate are known useful compounds.

Generally these materials are prepared by acid catalyzed reaction of the tertiary olefin with acetic acid in order to avoid the formation of water and the corresponding equilibrium problems associated with acid-alcohol reactions. See U.S. Pat. Nos. 3,031,495, 3,053,887, 3,173,943, 3,172,905, 3,082,246 and 2,678,332. However, this technology has the problem of olefin polymerization which results in yield loss and purification difficulties. The formation of t-alkyl esters by reaction of the tertiary alkanol with acetic anhydride has been considered but has not found widespread acceptance because it is a slow reaction even when carried out at reflux conditions. The use of catalysts such as Lewis acids or protic acids to improve reaction rates introduces problems of byproduct formation, e.g. alcohol dehydration. U.S. Pat. No. 6,593,491 discloses the formation of t-butyl acetate by reaction of acetic acid, acetic anhydride and MTBE or ETBE with an acid catalyst.

There is a need for a process for the production of t-alkyl esters which is rapid and selective and which lends itself to the ready recovery of reaction products and the recycle of unreacted materials.

Now it has been found that t-butyl acetate and t-amyl acetate can be readily formed in high selectivity and yield by reaction of the t-alkanol with acetic anhydride provided certain catalysts are used and provided that acetic acid is present.

BRIEF DESCRIPTION OF THE INVENTION

In accordance with the invention, acetic anhydride is reacted with t-butanol or t-amyl alcohol to produce the t-butyl or t-amyl acetate in high yield and with very high selectivity using tertiary amino catalysts such as dimethylamino pyridine and/or 1-methylimidazole as catalysts. Products of the reaction such as acetic acid and t-alkyl ester are recovered with recycle of unreacted anhydride together with catalyst. It is essential that acetic acid be present during the reaction in order to present decomposition of reaction components.

DESCRIPTION OF THE DRAWING

The accompanying drawing illustrates practice of the invention.

DETAILED DESCRIPTION

The acetic anhydride employed in the process of the invention is that which is produced commercially as by methyl acetate carbonylation or equivalent means.

The t-butanol and t-amyl alcohol reactants are also those which are available commercially, for example, from the Oxirane propylene oxide/t-butanol process. In especially preferred practice the t-alkanol is first purified by removal of impurities before reaction with acetic anhydride. The purification procedures taught in U.S. Pat. No. 6,417,412 and U.S. Pat. No. 6,770,790 can be used, the disclosures of these are incorporated herein by reference. Purification of the t-alkanol before reaction with the anhydride avoids problems of downstream purification where separation of impurities is not always convenient.

It is essential that acetic acid in amount of at least 5 wt % of the reaction mixture be present during the entirety of the reaction. It has been found that severe decomposition of system components takes place where acetic acid is not present throughout.

The reaction is preferably carried out in the liquid phase although vapor phase procedures can be used. Generally, mole ratios of alkanol to anhydride of 1:100 to 100:1 can be used with ratios of 5:1 to 1:5 mols alkanol per mol acetic anhydride being preferred.

The reaction is suitably carried out at temperatures in the range 0° C. to 400° C. with temperatures of 30° C. to 130° C. preferred. At lower temperatures the reaction is slow and at higher temperatures decomposition of various components of the systems tends to occur. Pressures of 0 psig to 100 psig are useful, preferably the pressure being sufficient to maintain the liquid phase.

Reaction time is generally of the order of 0.1 to 4.0 hours to provide acceptable conversions of t-alkanol and anhydride to make separation of tertiary butyl acetate simple.

Solvents such as saturated hydrocarbons can be employed but use of these is not necessary or preferred. It is advantageous to recycle a mixed acetic anhydride/acetic acid stream from product recovery to the esterification thus avoiding rigorous separation of acetic acid from the product mixture as well as providing the acetic acid necessary during the reaction. Essential to practice of the invention is the use of a tertiary amine catalyst, preferably a dialkylamino pyridine (e.g. dimethylamino pyridine) and/or a 1-alkylimidazole (e.g. 1-methylimidazole) catalyst. Through use of these catalysts a very rapid and highly selective reaction to produce the product tertiary alkyl acetate ester is achieved. In addition, use of these catalysts allows for the convenient recycle of acetic acid. Alternatively, solid catalysts comprised, for example, of the active catalyst components on a solid support such as a polystyrene/divinyl benzene can be used. Also the reaction product of chloromethylated polystyrene with the imidazole is an active catalyst.

The catalysts are stable and readily recovered and recycled. An outstanding advantage resides in the fact that the catalysts being basic do not promote dehydration of the t-alkanol to the olefin which would introduce a myriad of problems.

An outstanding advantage of the invention is that the reaction proceeds quickly and cleanly in accordance with the following equation without significant formation of byproducts:

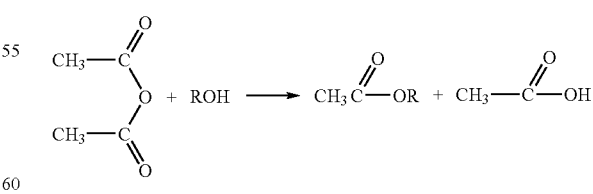

where R is t-butyl or t-amyl.

Referring to the drawing, in the preferred practice illustrated there is introduced to reaction zone 1 net t-butanol and acetic anhydride via line 2 as well as a recycle stream comprised of acetic anhydride and catalyst together with acetic acid via line 3.

In zone 1, illustrative reaction temperatures are 90 to 120° C., reaction pressure is 0 to 20 psig and residence time is 20 to 240 minutes. Feed to zone 1 comprises, on a mole basis, 1-5 moles TBA, 5-25 mols acetic anhydride and 0.1-2 moles catalyst. Acetic acid is essential and must comprise about at least 5 wt % of the reactor feed. It usually preferred to employ acetic anhydride in a molar ratio of at least 2:1 relative to TBA.

Reaction product is removed from zone 1 via line 4 and passes to distillation zone 5. A lighter boiling product tertiary butyl acetate stream is recovered via line 6 in amount of 1-5 moles.

A net acetic acid stream passes from distillation zone 5 via line 7 while a recycle stream comprised of 4-20 moles acetic anhydride, 1-5 moles acetic acid and 0.1-2 moles catalyst is recycled via line 3 to reaction zone 1.

It is distinctly advantageous to only partially separate acetic acid and acetic anhydride by distillation since such a separation is much less expensive than a complete separation. Acetic acid is necessary during the reaction in reactor 1 in order to avoid catalyst decomposition and this is conveniently provided by recycle to the esterification step of a mixture of acetic acid and acetic anhydride. As the following examples indicate, it is particularly necessary to have acetic acid in the reaction zone 1.

EXAMPLES

Comparative Example A

As a comparative example, 60 gm acetic anhydride and 4 gm 4-dimethylaminopyridine (DMAP) were heated under nitrogen to reflux temperature, 130° C. The solution turned black over 1 hour and the reactor contents analyzed as 6.27% acetone, 15.3% acetic acid, and several heavy unknown peaks.

This illustrates the extreme instability of the DMAP catalyst/acetic anhydride mixture in the absence of acetic acid.

Comparative Example B 60 gm of acetic anhydride was mixed with 24 gm acetic acid and 4 gm DMAP. The solution was refluxed under nitrogen for 3 hours. The clean water-white solution showed only 0.18% acetone made and acetic anhydride and DMAP as the only other organics product. This example shows that acetic acid is sufficient to eliminate the decomposition of acetic anhydride with DMAP catalyst to allow effective recycle of heavies as illustrated in the Figure.

Comparative Example C 1 mole, 74 gm, TBA was reacted with 5 moles of acetic anhydride and 10 gm DMAP in a batch mode. The mixture was kept at reflux for 1 hour, 115-120° C. GC analyses show almost 100% TBA conversion, <0.27% isobutylene make and a >50% increase in acetone indicating substantial catalyst/acetic anhydride decomposition.

Example 1

5 moles acetic anhydride, 2 moles crude TBA, 19 gm DMAP and 2 moles acetic acid were added to a batch reactor and heated to reflux for 2 hours, 110-113° C. Less than 0.17% isobutylene was made and acetone levels remained constant which indicated stability of the catalyst/acetic anhydride mixture when sufficient acetic acid is present. The TBA conversion was 94%.

Example 2

37 gm (0.5 mole) TBA, 0.4 moles acetic anhydride, and 6 gm acetic acid were heated with 1.94 g NMI at reflux for 3 hours, 98-102° C. The light yellow solution showed no change in acetone level, less than 0.17% isobutylene made, 92% acetic anhydride conversion and 99% TBAC selectivity.

Example 2 shows the reaction conducted with excess alcohol.

Comparative Example D 0.1 mole TBA and 0.5 mole acetic anhydride was heated with 4 gm NMI for 1 hour. The dark red-brown solution showed almost a four-fold increase in acetone during this time indicating severe catalyst decomposition.

Comparative Example E 100 gm of acetic acid and with 4 gm NMI 10 gm acetic anhydride were refluxed for 2 hours to give a clean solution with no evidence of acetone made or other degradation of anhydride or catalyst. This shows stability of the NMI/acetic anhydride where acetic acid is present.

Comparative Example F 20 gm of acetic anhydride and 1 gm of NMI were heated to reflux for 5 minutes to yield a black solution. GC analysis showed acetone and many heavy unidentified products demonstrating severe instability of the system in the absence of acetic acid.

The following examples further illustrate various features of the invention:

In a series of examples, tertiary butyl alcohol (TBA) was reacted with acetic anhydride to form tertiary butyl acetate (TBA) using either 1-methyl imidizole (NMI) or dimethylamino pyridine (DMAP) as catalyst. The feed materials were charged to a reactor and reacted at 100° C. The reaction mixtures were analyzed by GC after 30 minutes and after 60 minutes. The reactor charge for each example and the analysis results are given in the following Table I.

TABLE I

|  | Example G | Example H | Example I | Example 4 |
|---|---|---|---|---|
| Reactor Charge |  |  |  |  |
| Moles TBA | 0.1 | 0.1 | 0.1 | 0.1 |
| Moles acetic anhydride | .5 | .5 | .5 | .5 |
| Moles catalyst | .048 | .025 | .008 | .025, +.05 mol acid |

TABLE I-continued

|  | Example G | Example H | Example I | Example 4 |
|---|---|---|---|---|
| Catalyst | NMI | NMI | DMAP | NMI |
| 30 min GC, wt % | | | | |
| TBA | 0.85 | 3.3 | 3.6 | 2.89 |
| Acetic acid | 14.2 | 12.6 | 12.3 | 16.3 |
| TBAc | 30.8 | 29.6 | 28.8 | 28 |
| Acetic anhydride | 54 | 54.3 | 55.1 | 53 |
| 60 min GC, wt % | | | | |
| TBA | 0.18 | .54 | .86 | .58 |
| Acetic acid | 14.3 | 13.6 | 13.4 | 16.3 |
| TBAc | 32.5 | 32.6 | 31.1 | 31 |
| Acetic anhydride | 53 | 53 | 54 | 51 |
| Product Color | Brown | Yellow | Yellow | Water White |

In the above Table, Examples G-I are comparative, while Example 4 is in accordance with the invention.

These results demonstrate that tertiary butyl acetate can be rapidly and efficiently prepared by the reaction of tertiary butanol and acetic anhydride provided dimethylamino pyridine or 1-methylimidazole is used as catalyst and the improvement with added acid.

By way of contrast, in the absence of catalyst or employing conventional acidic catalyst at reflux, substantial yields of isobutylene are obtained.

An example illustrating the overall process in a continuous manner as shown in the drawing is as follows:

In a continuous system 2 moles acetic anhydride and 2 moles TBA are continuously fed per hour to reactor 1 via line 2 to which a recycle stream containing 3 moles per hour acetic anhydride, 2 moles per hour acetic acid and 0.1 moles per hour DMAP is fed via line 3 to reactor 1.

Conditions maintained in reactor 1 are 120° C. reaction temperature, 30 psig reaction pressure, 120 minutes residence time.

The reaction mixture is continuously passed via line 4 to distillation column 5, a tert-butyl acetate distillation product is removed via line 6 at a rate of 2 moles per hour at 98° C. and 0 psig, a distillate acetic acid stream is removed via line 7 at the rate of 2 moles per hour and 118° C. and a mixed stream comprised of 3 moles per hour acetic anhydride, 2 moles per hour acetic acid and 0.1 moles per hour DMAP are recycled to reactor 1 via line 3.

Overall selectively to tertiary butyl acetate based on tertiary butanol is 99%.

I claim:

1. A process for the preparation of tertiary butyl acetate or tertiary amyl acetate wherein acetic anhydride is reacted with t-butyl alcohol or t-amyl alcohol in the presence of at least 5wt. % acetic acid during the entirety of the reaction.

2. The method of claim 1 wherein a mixture of acetic anhydride and acetic acid is recycled from product separation to the esterification reaction.

3. The method of claim 1 wherein a 1-alkylimidazole catalyst is used.

4. The method of claim 1 wherein a dialkylamino pyridine catalyst is used.

5. The method of claim 1 wherein 1-methylimidazole catalyst is used.

6. The method of claim 1 wherein a dimethylamino pyridine catalyst is used.

* * * * *